US010099985B2

(12) United States Patent
Kurosawa et al.

(10) Patent No.: US 10,099,985 B2
(45) Date of Patent: Oct. 16, 2018

(54) METHOD FOR PRODUCING KETONE AND/OR ALCOHOL, AND SYSTEM THEREOF (71) Applicant: Ube Industries, Ltd., Ube-shi, Yamaguchi (JP)

(72) Inventors: Kazunori Kurosawa, Ube (JP); Yoshinori Sugimura, Ube (JP); Hideo Shimomura, Ube (JP); Kazuo Yamato, Ube (JP); Joji Funatsu, Ube (JP); Naoya Katagiri, Ube (JP); Junichi Kugimoto, Ube (JP); Joji Kawai, Bangkok (TH)

(73) Assignee: UBE INDUSTRIES, LTD., Ube-Shi (JP)

( * ) Notice: Subject to any disclaimer, the term of this patent is extended or adjusted under 35 U.S.C. 154(b) by 0 days.

(21) Appl. No.: 15/523,332

(22) PCT Filed: Oct. 5, 2015

(86) PCT No.: PCT/JP2015/078250
§ 371 (c)(1),
(2) Date: Jul. 13, 2017

(87) PCT Pub. No.: WO2016/067844
PCT Pub. Date: May 6, 2016

(65) Prior Publication Data
US 2017/0313641 A1 Nov. 2, 2017

(30) Foreign Application Priority Data
Oct. 31, 2014 (JP) .................. 2014-222348

(51) Int. Cl.
C07C 45/53 (2006.01)
C07C 29/00 (2006.01)
B01J 19/24 (2006.01)
B01J 23/75 (2006.01)
C07C 29/132 (2006.01)
C07C 35/08 (2006.01)
C07C 49/403 (2006.01)
B01J 19/18 (2006.01)
C07B 61/00 (2006.01)

(52) U.S. Cl.
CPC .......... C07C 45/53 (2013.01); B01J 19/1881 (2013.01); B01J 19/24 (2013.01); B01J 19/2415 (2013.01); B01J 19/2465 (2013.01); B01J 23/75 (2013.01); C07C 29/132 (2013.01); C07C 35/08 (2013.01); C07C 49/403 (2013.01); B01J 2219/00006 (2013.01); B01J 2219/00177 (2013.01); B01J 2219/24 (2013.01); C07B 61/00 (2013.01); C07C 2601/14 (2017.05)

(58) Field of Classification Search
CPC ......... C07C 45/53; C07C 29/132; B01J 19/24

USPC .................................... 568/342, 835
See application file for complete search history.

(56) References Cited

U.S. PATENT DOCUMENTS 4,704,476 A * 11/1987 Hartig ............... C07C 45/33
568/342
5,859,301 A * 1/1999 Kragten ............. C07C 29/132
568/311
7,956,221 B2 * 6/2011 Toth .................. C07C 29/132
568/342

FOREIGN PATENT DOCUMENTS

| EP | 0004105 A1 | 9/1979 |
| EP | 2096097 A1 | 9/2009 |
| JP | S5359650 A | 5/1978 |
| JP | S58192839 A | 11/1983 |
| JP | 62-169738 A | 7/1987 |
| JP | H05-025069 A | 2/1993 |
| JP | H09194408 A | 7/1997 |
| JP | H10-001449 A | 1/1998 |
| JP | 2004059515 A | 2/2004 |
| JP | 2004059515 A | 4/2004 |

(Continued)

OTHER PUBLICATIONS

WIPO, Japan Patent Office, International Search Report and Written Opinion dated Jan. 19, 2016 in International Patent Application No. PCT/JP2015/078250, 9 pages.

(Continued)

Primary Examiner — Sikarl A Witherspoon
(74) Attorney, Agent, or Firm — Knobbe Martens Olson & Bear LLP (57) ABSTRACT This invention provides producing having an objective ketone and/or alcohol by decomposing of a hydrocarbon compound rapidly and selectively having a same number of carbon atoms as a hydrocarbon compound by decomposing a hydroperoxide in a reaction solution obtained from oxidizing the hydrocarbon compound using molecular oxygen of this invention involves, a hydroperoxide decomposition step for decomposing the hydroperoxide into the ketone and/or alcohol by contacting the reaction solution with an aqueous solution containing a carbonate of an alkaline earth metal or a carbonate of an alkali metal and a transition metal compound, a separation step for separating into an oil phase comprising the ketone and/or alcohol, and a water phase comprising the carbonate of an alkaline earth metal or carbonate of an alkali metal and the transition metal compound, a recovery step for recovering the carbonate of an alkali metal or carbonate of an alkaline earth metal and the transition metal compound by combusting the water phase, and a recycling step for recycling to the hydroperoxide decomposition step by dissolving at least the carbonate of the alkali metal or the carbonate of the alkaline earth metal among the recovered substances obtained from the recovery step in water.

8 Claims, 1 Drawing Sheet (56) References Cited

FOREIGN PATENT DOCUMENTS

| | | |
|---|---|---|
| JP | 2005528455 A | 9/2005 |
| JP | H2007-223933 A | 9/2007 |
| JP | H2007-320878 A | 12/2007 |
| WO | WO2008/069127 A1 | 6/2008 |

OTHER PUBLICATIONS

Extended Search Report in European Patent Application No. 15853831.4, dated Jun. 18, 2018.

* cited by examiner

METHOD FOR PRODUCING KETONE AND/OR ALCOHOL, AND SYSTEM THEREOF

RELATED APPLICATIONS

This application is the U.S. National Phase of and claims priority to International Patent Application No. PCT/JP2015/078250, International Filing Date Oct. 5, 2015, entitled Method For Producing Ketone And/Or Alcohol, And System Thereof; which claims benefit of Japanese Application No. JP2014-222348 filed Oct. 31, 2014; both of which are incorporated herein by reference in their entireties.

TECHNICAL FIELD

The present invention pertains to a method for producing ketone and/or alcohol by oxidizing a hydrocarbon compound with molecular oxygen, wherein a hydroperoxide produced as an intermediate is decomposed to produce the ketone and/or alcohol, and pertains to a system thereof.

BACKGROUND

Oxidization of hydrocarbon compounds through molecular oxygen, and particularly oxidation through air have been examined for many years, and numerous methods have been disclosed. In the autoxidation of hydrocarbon compounds, the oxidation of cyclohexane is particularly important from an industrial perspective. The obtained cyclohexanone and cyclohexanol are very important compounds as raw materials for nylon 6 and nylon 6,6.

The oxidation of hydrocarbon compounds through molecular oxygen progresses via the corresponding hydroperoxide. The selectivity of an oxidation reaction from a hydrocarbon compound to a hydroperoxide is high, but under oxidation reaction conditions, hydroperoxides decompose into various byproducts other than the targeted alcohol and ketone, and therefore the selectivity decreases. In order to prevent this decrease in selectivity, a method is generally adopted in which the oxidation reaction is ended at a stage in which the conversion is low, and the hydroperoxides in the reaction solution that remain without decomposing are decomposed at the next step to produce the target ketone and/or alcohol.

Methods for decomposing hydroperoxides can be broadly categorized into two types of methods. The first is a method which adds a small amount of a transition metal compound or the like to decompose the hydroperoxide, and the second is a method which causes contact with an alkaline aqueous solution to decompose the hydroperoxide.

Of these, with the first type of method, the rate of decomposition of the hydroperoxide is slow, and the decomposition selectivity is also not very high, and therefore ordinarily the second type of method is adopted.

Note that with the process of the second type of method, the neutralization of carboxylic acid produced as a byproduct by the oxidation reaction, and the hydrolysis of esters produced as byproducts by the same oxidation reaction are simultaneously performed, and therefore this is known as a saponification step.

In the saponification step, hydroperoxide is decomposed with high selectivity, and therefore it is crucial that hydroperoxide be moved rapidly to the alkaline water phase. This is because radical decomposition of hydroperoxides having low selectivity progresses in the oil phase, and the decomposition selectivity decreases. With the saponification step, hydroperoxides are rapidly moved to the water phase, and detached, and therefore a strong alkaline aqueous solution such as alkali metal hydroxides or the like is used. However, the carboxylic acids produced in the oxidizing step reduce the pH of the saponification step. In order to prevent this, a method is widely adopted in which the saponification step is divided into two steps: a carboxylic acid neutralization step and a hydroperoxide decomposition step, and the oxidation reaction solution and the alkaline aqueous solution are brought into contact. This is called a two-step saponification process. However, the alkaline water phase that is discharged from the carboxylic acid neutralization step has a low pH value, and therefore this cannot be recirculated and used.

It is also difficult to recycle and reuse the strong alkali. Namely, with the two-step saponification process, the consumption of alkali necessary for at least the neutralization of carboxylic acid and the hydrolysis of ester in the process cannot be avoided.

On the other hand, if an alkali metal carbonate such as sodium carbonate is used as the alkali, the alkali metal carbonate can be regenerated and recycled by combusting the alkaline water phase that is discharged. However, the pH of the alkali metal carbonate aqueous solution is significantly lower than the pKa (inverse logarithm of the acid dissociation constant of 12~13) of the hydroperoxide, and there is almost no effect of causing the hydroperoxide to dissociate and move to the alkaline water phase. Accordingly, with saponification through an alkali metal carbonate aqueous solution, the decomposition rate of the hydroperoxide is slower and the decomposition selectivity is lower compared to two-step saponification using a strong alkali. Moreover, the ketone/alcohol ratio of the ketone and alcohol that are produced is also lower than that of the two-step saponification using a strong alkali, and when the purpose is to obtain a ketone, the production of a ketone through the dehydrogenation of an alcohol becomes necessary, which is also disadvantageous.

PRIOR ART DOCUMENTS

Patent Documents

Patent Document 1: Japanese Unexamined Patent Application Publication No. S58-192839
Patent Document 2: Japanese Unexamined Patent Application Publication No. S53-59650
Patent Document 3: Japanese Unexamined Patent Application Publication No. H9-194408
Patent Document 4: Published Japanese Translation of PCT Application No. 2005-528455
Patent Document 5: Japanese Unexamined Patent Application Publication No. 2004-59515

SUMMARY OF THE INVENTION

Problem to be Solved by the Invention

An object of the present invention is to provide a method to rapidly and highly selectively decompose a hydroperoxide, obtained by oxidizing a hydrocarbon compound with molecular oxygen, using an alkaline aqueous solution for inexpensively producing a corresponding target ketone and/or alcohol by recovering and recycling the alkali, and to provide a system thereof. More particularly, an object of the present invention is to provide a method for inexpensively producing a ketone, and a system thereof.

The present invention pertains to the following matters.

1. A method for producing a ketone and/or alcohol having a same number of carbon atoms as the hydrocarbon compound by decomposing a hydroperoxide in a reaction solution obtained from oxidizing the hydrocarbon compound using molecular oxygen; wherein the method including:

a hydroperoxide decomposition step for decomposing the hydroperoxide into a ketone and/or alcohol by contacting the reaction solution with an aqueous solution containing a carbonate of an alkaline earth metal or a carbonate of an alkali metal and a transition metal compound;

a separation step for separating into an oil phase containing the ketone and/or alcohol, and a water phase containing the carbonate of an alkaline earth metal or carbonate of an alkali metal and the transition metal compound;

a water phase recycling step for recycling a part of the water phase to the hydroperoxide decomposition step;

a recovery step for recovering the carbonate of an alkali metal or carbonate of an alkaline earth metal and the transition metal compound by combusting at least a part of the remainder of the water phase; and an alkali recycling step for recycling to the hydroperoxide decomposition step by dissolving at least the carbonate of the alkali metal or the carbonate of the alkaline earth metal among the recovered substances obtained from recovery step in water.

2. The production method according to item 1, further including a concentration step for concentrating the water phase between the separation step and the recovery step.

3. The production method according to any one of items 1 or 2, wherein the pH of the water phase is more than or equal to 7.5 and less than or equal to 12.

4. The production method according to any one of items 1 to 3, wherein the transition metal compound includes at least one transition metal selected from a group including group 6A, group 7A, and group 8 of the periodic table of elements.

5. The production method according to any one of items 1 to 4, wherein the transition metal compound includes at least one transition metal selected from a group including chromium, manganese, iron, cobalt, nickel, copper, ruthenium, rhodium, palladium, and platinum.

6. The production method according to any one of items 1 to 5, wherein the transition metal compound is at least one type of compound selected from a group including mineral acid salts, carboxylates, carbonates, basic carbonates, hydroxides, oxides, and complexes.

7. The production method according to any one of items 1 to 6, wherein the hydrocarbon compound is cyclohexane, and the hydroperoxide is cyclohexyl hydroperoxide.

8. A system for producing a ketone and/or alcohol having a same number of carbon atoms as the hydrocarbon compound by decomposing a hydroperoxide in a reaction solution obtained from oxidizing the hydrocarbon compound using molecular oxygen; wherein the system including:

a hydroperoxide decomposition unit for decomposing the hydroperoxide into a ketone and/or alcohol by contacting the reaction solution with an aqueous solution containing a carbonate of an alkaline earth metal or a carbonate of an alkali metal and a transition metal compound;

a separation unit for separating into an oil phase containing the ketone and/or alcohol, and a water phase containing the carbonate of an alkaline earth metal or carbonate of an alkali metal and the transition metal compound;

a water phase recycling unit for recycling a part of the water phase to the hydroperoxide decomposition unit;

a recovery unit for recovering the carbonate of an alkali metal or carbonate of an alkaline earth metal and the transition metal compound by combusting at least a part of the remainder of the water phase; and an alkali recycling unit for recycling to the hydroperoxide decomposition unit by dissolving at least the carbonate of the alkali metal or the carbonate of the alkaline earth metal among the recovered substances obtained from the recovery in water.

Effect of the Invention

According to the present invention, a hydroperoxide obtained from oxidizing a hydrocarbon compound with molecular oxygen can be rapidly and highly selectively decomposed to produce a target ketone and/or alcohol. Also according to the present invention, a carbonate of an alkaline earth metal or alkali metal can be recovered and recycled at a high yield, and therefore a method for inexpensively producing a target ketone and/or alcohol can be provided. In particular, according to the present invention, a method for inexpensively producing ketones can be provided.

BEST MODE FOR CARRYING OUT THE INVENTION

Figure 1:
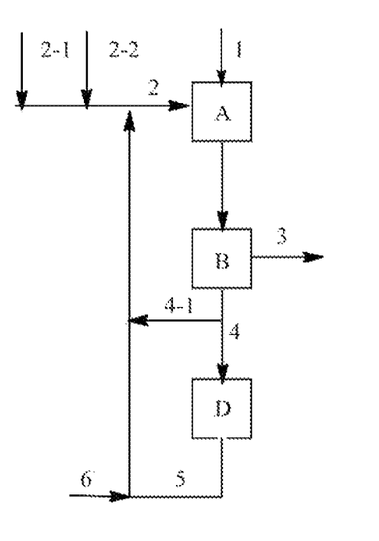
FIG. 1 is a basic flow chart of the present invention.

The present invention is described in detail as follows.

A hydroperoxide of the present invention is not particularly limited as long as it is the hydroperoxide of a hydrocarbon compound such as a chain-type hydrocarbon, an alicyclic hydrocarbon, or the like. Furthermore, the hydrocarbon compound may have a substituent. Examples include hydroperoxides of hydrocarbon compounds having from 5 to 20 carbon atoms such as cyclopentane, cyclohexane, cycloheptane, cyclooctane, cyclononane, cyclodecane, cyclododecane, cyclopentadecane, cyclohexadecane, and the like. Moreover, a mixture of hydroperoxides obtained by co-oxidizing two or more types of hydrocarbon compounds may also be used. For example, from cyclododecyl hydroperoxide and cyclohexyl hydroperoxide obtained by oxidizing a cyclohexane solution of cyclododecane, laurolactam and caprolactam can be coproduced, which are the raw materials of nylon 12 and nylon 6 ultimately.

Hydroperoxide can be produced by subjecting a corresponding hydrocarbon compound to an oxidation reaction using molecular oxygen without a solvent or in the presence of a solvent. For example, cycloalkyl hydroperoxide can be obtained by subjecting cycloalkane to a liquid phase contact reaction with molecular oxygen such as air under conditions including a reaction temperature of 120 to 180° C. and a reaction pressure of 1 to 20 atm.

As the solvent, the raw material hydrocarbon compound, or benzene, toluene, or the like can be used. With the present invention, the oxidation reaction solution can be used as is, or can be concentrated and used.

The oxidation reaction of the hydrocarbon compound through molecular oxygen is generally performed at a low conversion.

The reaction thereof is limited to a low conversion in order to prevent the successive oxidation of the ketones and alcohol, which are more easily oxidized than the hydrocarbon compound starting material, and to prevent the production of byproducts of higher order oxides such as carboxylic acid.

Moreover, a method in which an oxidation reaction is carried out without adding transition metal compound such as cobalt or other ordinarily used as an oxidation catalyst (referred to as uncatalytic oxidation method), and a method in which decomposition of the hydroperoxide in the oxidizing step is suppressed by adding a hydroperoxide stabilizer such as phosphoric acid ester (for example, Japanese Unexamined Patent Application Publication No. S62-120359) and then in the next step (hydroperoxide decomposition step), decomposing the hydroperoxide in a non-oxidizing atmosphere are adopted.

Furthermore, in order to prevent decomposition of the hydroperoxide through stainless steel, which is the material of the reaction vessel, a method for deactivating the surface of the reaction vessel with pyrophosphate or the like, and furthermore, a method for coating the oxidation reaction device with PFA (tetrafluoroethylene-perfluoro alkylvinyl ether copolymer) (for example, International Publication No. 2011-054809) may be used.

Decomposition of the hydroperoxide is performed under a non-oxidizing atmosphere, but radical decomposition progresses in the oil phase. Radical decomposition is meager in terms of selectivity, and the decomposition selectivity of hydroperoxide is not high.

Moreover, the ketone that is the target substance is present at a relatively high concentration in the oil phase, and therefore oxidation of the ketone through hydroperoxide progresses, and higher order oxides are produced as byproducts from the ketone, and as a result, the hydroperoxide decomposition selectivity decreases further.

In other words, in order to decompose the hydroperoxide with high selectivity, the hydroperoxide must be selectively and rapidly moved to the alkaline water phase, and ionically decomposed in the alkaline water phase.

However, the oil-water distribution equilibrium constant $K_D$ of hydroperoxide ([hydroperoxide concentration in the oil phase]/[hydroperoxide concentration in the water phase]) is large, and the hydroperoxide is difficult to distribute in the water phase.

On the other hand, the hydrogen atom of ROO—H of hydroperoxide has an acidic property, and the acid dissociation constant ($K_a$) thereof is from $10^{-12}$ to $10^{-13}$. That is to say, in an alkaline aqueous solution with a pH of 13 or higher, hydroperoxide dissociates into the anion (ROO$^-$) thereof. Therefore, in the abovementioned pH range, the distribution ratio D ([hydroperoxide concentration in the oil phase]/[hydroperoxide+hydroperoxy anion concentration in the water phase]) decreases, and the hydroperoxide concentration in the oil phase decreases.

Furthermore, in an alkaline aqueous solution with a pH of 13 or higher, hydroperoxy anions rapidly decompose into the corresponding ketone and/or alcohol.

In order to replenish the decomposed hydroperoxy anions (to maintain the distribution ratio D of the oil phase and water phase at a constant level), the hydroperoxide in the oil phase rapidly moves into the alkaline water phase. Accordingly, the overall general decomposition rate of the hydroperoxide (rate of the entire process of substance movement, dissociation, and decomposition) accelerates remarkably. In other words, the hydroperoxide can be rapidly decomposed by bringing into contact with a strong alkali with a pH of 13 or higher. An alkali metal hydroxide aqueous solution is used as the strong alkali having a pH of 13 or higher.

Moreover, the $K_D$ values of the hydrocarbon compound and the corresponding ketone and alcohol are generally large, and the concentrations of these in the alkaline water phase are low. Accordingly, byproducts produced by the oxidation of these compounds by the hydroperoxide are minimal, and the hydroperoxide decomposition selectivity is high.

However, carboxylic acid and carboxylic acid esters produced as byproducts are present in the oxidation reaction solution, and alkali is consumed to neutralize and hydrolyze (saponify) those substances. Above all, the neutralization reaction of carboxylic acid proceeds at a significantly faster pace than the hydroperoxide decomposition reaction, and therefore the pH of the alkali metal hydroxide aqueous solution immediately decreases the moment that the oxidation reaction solution and the alkali metal hydroxide aqueous solution are contacted. Accordingly, large amounts of alkali metal hydroxides are necessary to maintain a high pH at the time of the hydroperoxide decomposition reaction. The method for decomposing hydroperoxide while maintaining a high pH with as little an amount of alkali metal hydroxides as possible is the two-step saponification process. However, even with the two-step saponification process, an amount corresponding to the amount of alkali metal hydroxides that are consumed with the neutralization and saponification reactions must be newly added. In other words, the two-step saponification process excels in terms of the hydroperoxide overall decomposition rate and decomposition selectivity, but is not a process that is satisfactory in terms of the consumption of alkali metal hydroxides.

The water phase discharged from the hydroperoxide decomposition step (waste alkali) contains an alkali metal salt of a carboxylic acid. The only method that is ordinarily and industrially implementable for recovering alkali metal from waste alkali is a method of combustion. A carbonate of an alkali metal is obtained by combusting alkali metal salts of carboxylic acids. However, the alkali metal carbonate is thermally stable, and decomposition into an alkali metal oxide and carbon dioxide is difficult. The pH of the alkali metal carbonate aqueous solution is at most 12, and is lower than the pKa of the hydroperoxide.

Accordingly, even if hydroperoxide decomposition is performed with an aqueous solution of an alkali metal carbonate, a sufficient overall decomposition rate cannot be obtained. Therefore, because reactions such as radical decomposition of the hydroperoxide in the oil phase and oxidation of ketones due to the hydroperoxide proceed, the hydroperoxide decomposition selectivity is low.

In order to resolve the abovementioned issues, the inventors of the present invention have found out a method for increasing the decomposition reaction rate and improving the overall decomposition rate by adding a catalyst to accelerate hydroperoxide decomposition in an aqueous solution of a carbonate of an alkaline earth metal or alkali metal as a result of keen examinations to solve the problem, and have completed the invention.

The mass transfer rate constant of the hydroperoxide from the oil phase to the alkaline water phase is considerably larger than the hydroperoxide decomposition rate constant.

Accordingly, even in the low pH range, or in other words, in the range at which the distribution ratio D of the hydroperoxide is large, if the hydroperoxide decomposition reaction rate is increased, the general decomposition rate can be improved.

In other words, even if an alkali metal carbonate aqueous solution is used, a sufficient overall decomposition rate and decomposition selectivity can be obtained, and a method for producing a ketone and/or alcohol for which the alkali metal can be recycled can be provided. The present invention can provide an excellent method capable of simultaneously reducing the hydrocarbon basic unit (weight of the hydrocarbon compound necessary to produce the unit weight of the target ketone and alcohol) and the alkali basic unit (weight of the alkali metal necessary to produce the unit weight of the target ketone and alcohol).

Furthermore, because ketones are preferentially produced, the load of the transformation step from an alcohol to a ketone can be reduced when acquisition of the ketone is the target.

Embodiments for carrying out hydroperoxide decomposition are described as follows.

An aqueous solution of alkali metal carbonates or alkaline earth metal carbonates can be used to decompose hydroperoxide, and preferably, the aqueous solution is one of alkali metal carbonates. For example, alkali metal carbonates include lithium carbonate, sodium carbonate, potassium carbonate and the like, and sodium carbonate is particularly preferable. A concentration of the alkali metal carbonate or alkaline earth metal carbonate in the aqueous solution of alkali metal carbonate or alkaline earth metal carbonate is not particularly limited as long as the concentration is less than or equal to the solubility, and in the case of sodium carbonate, the concentration of more than or equal to 5 weight % and less than or equal to 30 weight %, and preferably more than or equal to 15 weight % and less than or equal to 25 weight % is recommended. If the concentration is too high, in some cases a salt such as sodium bicarbonate with a lower solubility than sodium carbonate is deposited in the hydroperoxide decomposition step, and this is not preferable for driving devices. If the concentration thereof is too low, it is also not preferable because a large amount of energy is required in concentrating the later-described waste alkali. Furthermore the abovementioned aqueous solution may contain respectively two or more alkali metal carbonates or alkaline earth metal carbonates, or may contain both an alkali metal carbonate and an alkaline earth metal carbonate.

The used amount of alkali for decomposing hydroperoxide is not particularly limited as long as it is more than or equal to an equivalent to the total amount of the carboxylic acid and carboxylic acid ester in the oxidation reaction solution, the used amount thereof is preferably more than or equal to 1.0 equivalents and less than or equal to 2.0 equivalents, and more preferably more than or equal to 1.05 equivalents and less than or equal to 1.3 equivalents. If the used amount of alkali is too small, it is not preferable because decomposition of the hydroperoxide and esters does not sufficiently proceed. If the used amount of alkali is too much, it is not preferable because an excessive amount of energy is consumed in the alkali recovery step and the alkali basic unit increases.

Examples of transition metals which are used as the hydroperoxide decomposition catalyst are elements belonging to group 6A, group 7A, and group 8 of the periodic table of elements (note that names of the groups and periods of these elements are based on the long-period type periodic table of elements (1) of Appendix II of the 1993 $4^{th}$ Edition of the "Dictionary of Physics and Chemistry" from Iwanami Shoten).

Examples of transition metal include chromium, manganese, iron, cobalt, nickel, copper, ruthenium, rhodium, palladium, platinum, and the like. In these transition metals, chromium, iron, cobalt and copper have excellent hydroperoxide decomposition activity, and cobalt is a particularly preferable metal element.

The transition metal is, for example, added to the hydroperoxide decomposition step as a mineral acid salt, carboxylate, carbonate, basic carbonate, hydroxide, oxide, or complex. In these, mineral acid salts and carboxylates are preferable because those have high solubility in water and are easy to handle.

The concentration of the transition metal in the alkali phase (aqueous solution containing an alkaline earth metal carbonate or an alkali metal carbonate and a transition metal compound) is more than or equal to 0.1 weight ppm and less than or equal to 1000 weight ppm, and preferably more than or equal to 1 weight ppm and less than or equal to 100 weight ppm.

If the concentration of the transition metal concentration is too low, a remarkable effect of acceleration decomposition of hydroperoxide is not obtained. Furthermore, even if the transition metal concentration is too high, a effect of acceleration decomposition of hydroperoxide is not exerted higher than that, and it is not preferable because the transition metal catalyst is only consumed.

The temperature of the hydroperoxide decomposition step is more than or equal to 80° C. and less than or equal to 170° C., and preferably more than or equal to 100° C. and less than or equal to 150° C. If the temperature is too low, because the hydrolysis rate of the hydroperoxide and ester is slow, a long and large reaction tank is required for finishing these decomposition.

On the other hand, if the temperature is too high, it is not preferable because hydroperoxide decomposition selectivity decreases.

The pH of the alkali phase in the hydroperoxide decomposition step is important, the favorable pH is for example from 7.5 to 12, and preferably from 9 to 11. As described above, the distribution ratio D of the hydroperoxide is affected by the pH, and as the pH value is increased, the distribution ratio D of the hydroperoxide is decreased. In other words, the hydroperoxide becomes more easily distributed to the alkaline water phase. On the other hand, the transition metal compound forms hydroxides in the alkaline water phase, and the solubility thereof is low. The solubility of the hydroxides increases as the pH is lowered. Accordingly, from the perspective of distribution of the hydroperoxide into the alkali phase and solubility of the catalyst metal in the alkali phase, it is necessary to select an appropriate pH, and the range of the pH thereof is the abovementioned range.

To complete of hydroperoxide decomposition is an essential requirement of a retention time of the hydroperoxide decomposition step, the retention time of the hydroperoxide decomposition step differs depending on the temperature, type of catalyst and concentration in the alkali phase, pH of the alkali phase, oil/water ratio, oil/water mixing condition, and the like, but it is not preferable because requiring a long retention time means that a long and large reaction device is necessary. Accordingly, the reaction conditions are set such that the retention time is less than or equal to 2 hours, and is preferably less than or equal to 1 hour. On the other hand, the hydroperoxide decomposition reaction is an exothermic reaction, and therefore it is preferable that a retention time is more than or equal to 1 minute for the purpose of controlling the reaction.

The hydroperoxide decomposition device is not particularly limited, and by using an extraction column such as a perforated plate extraction column, rotating disc extraction column, pulsating perforated plate column, and vibration plate column, the hydroperoxide decomposition reaction and ester hydrolysis reaction, and the oil-water separation of the next step may be performed within a single device, or the reaction portion and the separatory portion may be performed within a separated device. In the case of the latter, for example, a stirring tank type reactor, a tubular type reactor, and a column type reactor are used in the reaction portion. inserting a static mixer or the like directly before the reactor for the purpose of mixing and dispersing the oil/water is a preferable aspect. For example, a settler, centrifuge device, liquid cyclone, and the like are used in the separatory portion. Among those, a combination of a static mixer, column type reactor, and settler is the most simple and easy device. Moreover, parts which promote separation such as a coalescer may be disposed inside the settler. The temperatures of the reaction step and the separatory step may be different, but ordinarily the temperatures are the same.

The retention time of the waste alkali separation step is preferably short so far as the oil/water separation is completed, and for example is more than or equal to 1 minute and less than or equal to 60 minutes, and is preferably more than or equal to 1 minute and less than or equal to 30 minutes. If the retention time is too short, in some cases it is difficult to operate control and separation of the oil phase and water phase is insufficient. If the retention time is too long, it is not preferable because a long and large is required.

The separated waste alkali is incinerated in a combustion furnace preferably with auxiliary fuel. As the auxiliary fuel, refined fossil fuels such as heavy oil and other may be used, but organic substance-containing liquid waste such as waste oil and other may be effectively used. The carboxylates and the like in the waste alkali is recovered as carbonates of alkaline earth metals or carbonates of alkali metal, and are dissolved in water to be recycled to the hydroperoxide decomposition step. In other words, this process is a process of recovering and recycling almost all of the alkaline earth metal carbonates or alkali metal carbonates, and theoretically is a process that does not require the new addition of alkaline earth metal carbonates or alkali metal carbonates. Note that examples of alkali recovery devices include submerged combustion devices, and the like.

On the other hand, the transition metals in the waste alkali are recovered as oxides. The recovered transition metal oxides may also be recycled with the abovementioned alkali metal carbonates to the hydroperoxide decomposition step, but if the solubility of the transition metal oxides in an alkaline aqueous solution is low and precipitation is generated, after the recovered transition metal oxides are separated from the alkali metal carbonate aqueous solution to be recycled, they may be dissolved once again in mineral acid or the like and adjusted to an appropriate pH, after which they may be recycled to the hydroperoxide decomposition step.

Note that with the present invention, it is a preferable aspect that a waste alkali concentration step inserts between the waste alkali separation step and the alkali recovery step, because it has the merits of reducing the fuel for combustion in the alkali recovery step and enabling a reduction in the size of the combustion furnace.

The waste alkali is concentrated by thin film evaporation, flash evaporation, and the like, and water is removed. Through concentration, the trace amounts of ketones and/or alcohol dissolved in the waste alkali can also be recovered with distilled water. Furthermore, by reusing the recovered water as water for dissolving the recovered alkali, another merit of reducing the hydrocarbon basic unit is also provided.

As the concentration ratio is increased, the abovementioned effect is more remarkably manifest, but operational problems such as an increase in the viscosity of the waste alkali concentrated liquid occur, and therefore, for example, operation at a concentration of more than or equal to 1.2 times and less than or equal to 10 times, and preferably at a concentration of more than or equal to 1.5 times and less than or equal to 5 times is favorable.

Moreover, a portion of the waste alkali and/or concentrated waste alkali are recycled to the hydroperoxide decomposition step. The waste alkali contains an alkali metal salt of a carboxylic acid. The alkali metal salts of long-chain carboxylic acids act as surfactants and increase the mass transfer rate of the hydroperoxide between oil and water. Moreover, the alkali metal salt of long-chain carboxylic acids also lowers the $K_D$ of the hydroperoxide and increases the distribution equilibrium concentration of the hydroperoxide in the water phase. Hence, the overall decomposition rate of the hydroperoxide improves. Furthermore, the alkaline earths or alkali metal salts of the carboxylic acid improve the solubility of the transition metal hydroxides. In other words, the effective catalyst concentration in the alkaline water phase increases, and the decomposition reaction rate of the hydroperoxide is increased. Through these effects, the overall decomposition rate of the hydroperoxide can be improved.

Furthermore, a portion of the transition metal catalyst is also recycled with the waste alkali and/or concentrated waste alkali. The transition metal in the waste alkali forms hydroxide, and the catalytic activity of hydroxide is higher than that of oxides. Accordingly, recycling of the waste alkali and/or concentrated waste alkali has an effect of decreasing the usage amount of transition metal compared to a process of circulating recovered alkali after combusting the entire amount of the waste alkali.

The recycled amount of the waste alkali and/or concentrated waste alkali is for example, more than or equal to 5% and less than or equal to 90%, and preferably more than or equal to 10% and less than or equal to 80% of the total amount. If the recycled amount is too small, the abovementioned recycling effect is not sufficiently exhibited. If the recycled amount is too large, it is not preferable because there is a possibility that byproducts will accumulate in the waste alkali, deposit on the reactor surface, and cause operational problems such as clogging of the pipelines.

Note that if transition metal hydroxides are deposited, the deposits may be filtered, and recycled to a hydroperoxide decomposition step separately.

On the other hand, as necessary, the oil phase (saponification liquid) separated in the waste alkali separation step recover the unreacted raw material of hydrocarbon compounds and/or oxidation reaction solvent, then is refined by a method of distillation or the like, and ketones and/or alcohols are obtained. Furthermore, as desired, in some cases, alcohol is dehydrogenated to obtain only ketones.

A system for producing ketones and/or alcohol is described as follows.

The system for producing ketones and/or alcohol of the present invention is a system for producing a ketone and/or alcohol having a same number of carbon atoms as the hydrocarbon compound by decomposing a hydroperoxide in a reaction solution obtained from oxidizing the hydrocarbon compound using molecular oxygen; wherein the system thereof including:

a hydroperoxide decomposition unit for decomposing the hydroperoxide into a ketone and/or alcohol by contacting the reaction solution with an aqueous solution containing a carbonate of an alkaline earth metal or a carbonate of an alkali metal and a transition metal compound;

a separation unit for separating into an oil phase containing the ketone and/or alcohol, and a water phase containing the carbonate of an alkaline earth metal or carbonate of an alkali metal and the transition metal compound;

a water phase recycling unit for recycling a part of the water phase to the hydroperoxide decomposition unit;

a recovery unit for recovering the carbonate of an alkali metal or carbonate of an alkaline earth metal and the transition metal compound by combusting at least a part of the remainder of the water phase; and an alkali recycling unit for recycling to the hydroperoxide decomposition unit by dissolving at least the carbonate of the alkali metal or the carbonate of the alkaline earth metal among the recovered substances obtained from the recovery in water.

(Hydroperoxide Decomposition Unit)

The hydroperoxide decomposition unit includes a decomposition reactor for contacting the oxidation reaction solution with an aqueous solution containing a carbonate of an alkaline earth metal or a carbonate of an alkali metal and a transition metal compound, and decomposing the hydroperoxide into the ketone and/or alcohol.

(Waste Alkali Separation Unit)

The waste alkali separation unit includes a separation tank for separating into an oil phase (hereinafter, referred to as a saponification liquid) containing the ketone and/or alcohol, and a water phase (hereinafter, referred to as a waste alkali) containing the carbonate of an alkaline earth metal or carbonate of an alkali metal and the transition metal compound.

(Water Phase Recycling Unit)

The water phase recycle unit includes pump and transportation line for recycle of waste alkali to hydroperoxide decomposition unit.

(Alkali Recovery Unit)

The alkali recovery unit includes a combustion furnace for combusting the waste alkali, and recovering the carbonate of an alkali metal or carbonate of an alkaline earth metal and the transition metal compound.

(Recovered Alkali Recycling Unit)

The recovered alkali recycling unit includes a dissolving tank for dissolving the recovered alkali in water, and piping for recycling the aqueous solution of the recovered alkali to the hydroperoxide decomposition unit.

Each of the abovementioned units is connected by piping to send the targeted substance sequentially to the next unit.

EXAMPLES

The present invention is described in greater detail below with the presentation of experiments relating to the decomposition of cyclohexyl hydroperoxide (CHP), which is produced by oxidizing cyclohexane (Cx) with molecular oxygen. However, the present invention is not limited to the following examples.

Note that the selectivity of the total (CxONOL) of cyclohexanone and cyclohexanol of Comparative Examples 5, Examples 7, Comparative Examples 6, Examples 8, and Comparative Examples 7 and 8 (decomposition experiments of refined cyclohexyl hydroperoxide) is determined by analyzing the cyclohexyl hydroperoxide (CHP), cyclohexanone (CxON), cyclohexanol (CxOL) and byproducts through use of gas chromatography and a total organic carbon meter, and by using the following equation. Note that the amount (moles) of solvent consumption is the molar amount obtained by subtracting the total molar amount of the CHP, CxON, and CxOL before the reaction from the total molar mount of the CHP, CxON, CxOL, and byproducts after the reaction (molar amount converted to a carbon count of 6).

CxONOL Selectivity (%)=[Amount of CxON produced (moles)+Amount of CxOL produced (moles)]/[Amount of CHP consumed (moles)+ Amount of solvent consumed (moles)]×100    [Equation 1]

Moreover, the total (CxONOL) selectivity of the cyclohexanone and cyclohexanol of Comparative Example 9, Examples 10 to 12 and Comparative Example 10 (decomposition experiments of cyclohexyl hydroperoxide in an oxidation reaction solution) is determined by the following equation.

CxONOL Selectivity (%)=[Amount of CxON produced (moles)+Amount of CxOL produced (moles)]/[Amount of CHP consumed (moles)+ Amount of solvent consumed (moles)+Amount of other peroxides consumed (moles)+Amount of other CxONOL precursors (moles)]×100    [Equation 2]

Here, the amount of other peroxides consumed is the peroxide consumption amount including cyclohexane rings detected by gas chromatography, and the amount of other CxONOL precursors is determined by subjecting the oxidation reaction solution to a triphenyl phosphine treatment, and then adding 17 weight % of a sodium carbonate aqueous solution, heating for 2 hours at 155° C., and then subtracting the amount of cyclohexyl peroxide consumed and the amount of other peroxides consumed from the amount of cyclohexanone increase and the amount of cyclohexanol increase.

[Cyclohexyl Peroxide Decomposition Acceleration Effect by Addition of Catalyst and Waste Alkali]

Comparative Example 1

Amounts of 450 g of cyclohexane and 40 g of a 17 weight % sodium carbonate aqueous solution containing 10 weight ppm of Co (cobalt) were charged into a 500 mL internal capacity reactor made of SUS with the surface coated with Teflon (registered trademark), and the materials were heated to 125° C. Fifty grams of a cyclohexane solution containing 20 weight % of cyclohexyl hydroperoxide, 10 weight % of cyclohexanone, and 20 weight % of cyclohexanol was pressed into this mixed liquid, and the cyclohexyl hydroperoxide decomposition rate was measured while obtaining samples at each prescribed time. The overall decomposition rate constant of the cyclohexyl hydroperoxide was 0.063 (1/minute), and the decomposition percentage after 20 minutes was 78.4%. Note that the pH of the water phase before the reaction was 11.9, and the pH of the water phase after the reaction was 10.7.

Example 1

The same reaction as that of Comparative Example 1 was carried out with the exception that the water phase charged into the SUS reactor contained 10 weight ppm of Co, 17 weight % of sodium carbonate, and 2.5 weight % of valeric acid. The overall decomposition rate constant of the cyclohexyl hydroperoxide was 0.226 (1/minute), and the decomposition percentage after 20 minutes was 99.7%. Note that the pH of the water phase before the reaction was 10.3, and the pH of the water phase after the reaction was 10.0.

Example 2

The same reaction as that of Comparative Example 1 was carried out with the exception that the water phase charged into the SUS reactor contained 10 weight ppm of Co, 17 weight % of sodium carbonate, and 2.5 weight % of caproic acid. The overall decomposition rate constant of the cyclohexyl hydroperoxide was 0.199 (l/minute), and the decomposition percentage after 20 minutes was 99.1%. Note that the pH of the water phase before the reaction was 10.3, and the pH of the water phase after the reaction was 10.0.

Example 3

The same reaction as that of Comparative Example 1 was carried out with the exception that the water phase charged into the SUS reactor contained 10 weight ppm of Co, 17 weight % of sodium carbonate, and 3.7 weight % of caproic acid. The overall decomposition rate constant of the cyclohexyl hydroperoxide was 0.222 (l/minute), and the decomposition percentage after 20 minutes was 99.8%. Note that the pH of the water phase before the reaction was 10.5, and the pH of the water phase after the reaction was 10.1.

Example 4

The same reaction as that of Comparative Example 1 was carried out with the exception that the water phase charged into the SUS reactor contained 10 weight ppm of Co, 17 weight % of sodium carbonate, and 5.1 weight % of caproic acid. The overall decomposition rate constant of the cyclohexyl hydroperoxide was 0.248 (l/minute), and the decomposition percentage after 20 minutes was 100%. Note that the pH of the water phase before the reaction was 10.5, and the pH of the water phase after the reaction was 10.1.

Example 5

The same reaction as that of Example 2 was carried out with the exception that a small amount of hydrochloric acid was added to the water phase charged into the SUS reactor to adjust the pH to 9.1. The overall decomposition rate constant of the cyclohexyl hydroperoxide was 0.110 (l/minute), and the decomposition percentage after 20 minutes was 88.1%. Note that the pH of the water phase after the reaction was 9.05.

Example 6

The same reaction as that of Example 2 was carried out with the exception that a small amount of sodium hydroxide was added to the water phase charged into the SUS reactor to adjust the pH to 12.0. The overall decomposition rate constant of the cyclohexyl hydroperoxide was 0.116 (l/minute), and the decomposition percentage after 20 minutes was 91.4%. Note that the pH of the water phase after the reaction was 10.75.

Comparative Example 2

The same reaction as that of Comparative Example 1 was carried out with the exception that Co was not contained in the water phase charged into the SUS reactor. The overall decomposition rate constant of the cyclohexyl hydroperoxide was 0.036 (l/minute), and the decomposition percentage after 20 minutes was 53.6%. Note that the pH of the water phase before the reaction was 11.9, and the pH of the water phase after the reaction was 9.9.

Comparative Example 3

The same reaction as that of Example 1 was carried out with the exception that Co was not contained in the water phase charged into the SUS reactor. The overall decomposition rate constant of the cyclohexyl hydroperoxide was 0.022 (l/minute), and the decomposition percentage after 20 minutes was 40.1%. Note that the pH of the water phase before the reaction was 10.3, and the pH of the water phase after the reaction was 9.6.

Comparative Example 4

The same reaction as that of Comparative Example 2 was carried out with the exception that a small amount of sodium hydroxide was added to the water phase charged into the SUS reactor to adjust the pH to 12.8. The overall decomposition rate constant of the cyclohexyl hydroperoxide was 0.042 (l/minute), and the decomposition percentage after 20 minutes was 56.8%. Note that the pH of the water phase after the reaction was 12.6.

The results of the abovementioned Examples 1 to 6 and Comparative Examples 1 to 4 are shown in the following Table 1 (CHP Decomposition rate Comparison Table).

TABLE 1

| | Alkali | Co Concentration (ppm) | Carbon Addition | pH Before Reaction | pH After Reaction | Decomposition Percentage After 20 Min. (%) | Overall decomposition rate Constant (1/min) |
|---|---|---|---|---|---|---|---|
| Comparative Example 1 | 17% $Na_2CO_3$ | 10 | Not added | 11.9 | 10.7 | 78.4 | 0.063 |
| Example 1 | 17% $Na_2CO_3$ | 10 | Valeric acid 2.5% | 10.3 | 10.0 | 99.7 | 0.226 |
| Example 2 | 17% $Na_2CO_3$ | 10 | Caproic acid 2.5% | 10.3 | 10.0 | 99.1 | 0.199 |
| Example 3 | 17% $Na_2CO_3$ | 10 | Caproic acid 3.7% | 10.5 | 10.1 | 99.8 | 0.222 |
| Example 4 | 17% $Na_2CO_3$ | 10 | Caproic acid 5.1% | 10.5 | 10.1 | 100.0 | 0.248 |
| Example 5 | 17% $Na_2CO_3$ + HCl | 10 | Caproic acid 2.5% | 9.1 | 9.05 | 88.1 | 0.110 |
| Example 6 | 17% $Na_2CO_3$ + NaOH | 10 | Caproic acid 2.5% | 12.0 | 10.75 | 91.4 | 0.116 |
| Comparative Example 2 | 17% $Na_2CO_3$ | Not added | Not added | 11.9 | 9.9 | 53.6 | 0.036 |
| Comparative Example 3 | 17% $Na_2CO_3$ | Not added | Valeric acid 2.5% | 10.3 | 9.6 | 40.1 | 0.022 |
| Comparative Example 4 | 17% $Na_2CO_3$ + NaOH | Not added | Not added | 12.8 | 12.6 | 56.8 | 0.042 |

[Effect of Improving Cyclohexyl Peroxide Decomposition Selectivity by Addition of Catalyst and Waste Alkali]

Comparative Example 5

Cyclohexyl hydroperoxide was decomposed under the same conditions as those of Comparative Example 1 with the exception that the water phase charged into the SUS reactor included 40 weight ppm of Co and 17 weight % of sodium carbonate, and the reaction time was 70 minutes. After the reaction was completed, the cyclohexyl hydroperoxide, cyclohexanone, cyclohexanol, and various byproducts in the oil phase and water phase were quantitatively determined, and the selectivity was calculated using [Equation 1]. The decomposition percentage of the cyclohexyl hydroperoxide was 100%, the cyclohexanone selectivity was 78.3%, the cyclohexanol selectivity was 13.8%, and the total selectivity of both was 92.1%. Moreover, the cyclohexanone/cyclohexanol production ratio was 5.66.

Example 7

Cyclohexyl hydroperoxide was decomposed under the same conditions as those of Example 1 with the exception that the Co concentration in the water phase charged into the SUS reactor was 40 weight ppm, and the reaction time was 40 minutes. The decomposition percentage of the cyclohexyl hydroperoxide was 100%, the cyclohexanone selectivity was 77.3%, the cyclohexanol selectivity was 17.2%, and the total selectivity of both was 94.5%. Moreover, the cyclohexanone/cyclohexanol production ratio was 4.51.

Comparative Example 6

Cyclohexyl hydroperoxide was decomposed under the same conditions as those of Comparative Example 5 with the exception that the reaction temperature was 155° C., and the reaction time was 20 minutes. The decomposition percentage of the cyclohexyl hydroperoxide was 100%, the cyclohexanone selectivity was 69.1%, the cyclohexanol selectivity was 19.9%, and the total selectivity of both was 89.0%. Moreover, the cyclohexanone/cyclohexanol production ratio was 3.48.

Example 8

Cyclohexyl hydroperoxide was decomposed under the same conditions as those of Example 7 with the exception that the reaction temperature was 155° C., and the reaction time was 10 minutes. The decomposition percentage of the cyclohexyl hydroperoxide was 100%, the cyclohexanone selectivity was 76.7%, the cyclohexanol selectivity was 15.7%, and the total selectivity of both was 92.4%. Moreover, the cyclohexanone/cyclohexanol production ratio was 4.89.

Example 9

Cyclohexyl hydroperoxide was decomposed under the same conditions as those of Example 8 with the exception that the Co concentration in the water phase was 10 weight ppm. The decomposition percentage of the cyclohexyl hydroperoxide was 100%, the cyclohexanone selectivity was 74.1%, the cyclohexanol selectivity was 18.9%, and the total selectivity of both was 93.0%. Moreover, the cyclohexanone/cyclohexanol production ratio was 3.93.

Comparative Example 7

Cyclohexyl hydroperoxide was decomposed under the same conditions as those of Comparative Example 2 with the exception that the reaction time was 360 minutes. The decomposition percentage of the cyclohexyl hydroperoxide was 100%, the cyclohexanone selectivity was 64.6%, the cyclohexanol selectivity was 22.8%, and the total selectivity of both was 87.3%. Moreover, the cyclohexanone/cyclohexanol production ratio was 2.83.

Comparative Example 8

Cyclohexyl hydroperoxide was decomposed under the same conditions as those of Comparative Example 7 with the exception that the reaction time was 300 minutes. The decomposition percentage of the cyclohexyl hydroperoxide was 96.9%, and cyclohexyl hydroperoxide remained. The cyclohexanone selectivity was 62.0%, the cyclohexanol selectivity was 21.8%, and the total selectivity of both was 83.8%. Moreover, the cyclohexanone/cyclohexanol production ratio was 2.84.

The results of the abovementioned Comparative Example 7, Examples 7, Comparative Examples 8 and 9, and Comparative Examples 7 and 8 are shown in the following Table 2 (CHP Decomposition Selectivity Comparison Table).

TABLE 2

| | Alkali | Co Concentration (ppm) | Carbon Addition | Reaction Temperature (° C.) | Reaction Time (min) | Decomposition Percentage (%) | Selectivity (%) | | | ON/OL |
| --- | --- | --- | --- | --- | --- | --- | --- | --- | --- | --- |
| | | | | | | | CxON | CxOL | CxONOL | |
| Comparative Example 5 | 17% Na$_2$CO$_3$ | 40 | Not added | 125 | 70 | 100 | 78.3 | 13.8 | 92.1 | 5.66 |
| Example 7 | 17% Na$_2$CO$_3$ | 40 | Valeric acid 2.5% | 125 | 40 | 100 | 77.3 | 17.2 | 94.5 | 4.51 |
| Comparative Example 6 | 17% Na$_2$CO$_3$ | 40 | Not added | 155 | 20 | 100 | 69.1 | 19.9 | 89.0 | 3.48 |
| Example 8 | 17% Na$_2$CO$_3$ | 40 | Valeric acid 2.5% | 155 | 10 | 100 | 76.7 | 15.7 | 92.4 | 4.89 |
| Example 9 | 17% Na$_2$CO$_3$ | 10 | Valeric acid 2.5% | 155 | 10 | 100 | 74.1 | 18.9 | 93.0 | 3.93 |
| Comparative Example 7 | 17% Na$_2$CO$_3$ | Not added | Not added | 125 | 360 | 100 | 64.6 | 22.8 | 87.3 | 2.83 |

TABLE 2-continued

| | Alkali | Co Concentration (ppm) | Carbon Addition | Reaction Temperature (° C.) | Reaction Time (min) | Decomposition Percentage (%) | Selectivity (%) | | | |
|---|---|---|---|---|---|---|---|---|---|---|
| | | | | | | | CxON | CxOL | CxONOL | ON/OL |
| Comparative Example 8 | 17% Na$_2$CO$_3$ | Not added | Not added | 125 | 300 | 96.9 | 62.0 | 21.8 | 83.8 | 2.84 |

[Effect by Addition of Catalyst and Waste Alkali when Oxidation Reaction Solution is Used in Raw Materials]

Comparative Example 9

An amount of 250 g of cyclohexane was added to a 500 mL SUS316L autoclave, and the internal temperature was heated to 157° C. while introducing nitrogen from a gas blow-in nozzle. After the internal temperature reached 157° C., the blow-in gas was switched to air, and a cyclohexane oxidation reaction was carried out for 107 minutes while air was blown in at a rate of 1 L/min.

The cyclohexane in the waste gas was condensed in a cooling pipe and flowed downward to the reactor, after which the concentrations of the carbon monoxide (CO) and carbon dioxide (CO$_2$) in the remaining waste gas were measured, and the amounts of CO and CO$_2$ that were produced were added. The abovementioned reaction was carried out in 12 batches. A portion of the reaction solution thereof was fractionated, gas chromatography (GC) analysis was performed, and the cyclohexanone, cyclohexanol, cyclohexyl hydroperoxide and byproducts (referred to as GC detected byproducts) were quantitatively determined.

Moreover, the carboxylic acid and the like produced as byproducts were extracted with a weak alkaline aqueous solution, the amount of the GC detected byproducts was subtracted from the measured value for the total organic carbon (TOC) in the water phase, and the water-soluble byproducts (converted to a molar amount of cyclohexane) were quantitatively determined.

The cyclohexane conversion and product yield were calculated using the following equations.

Cyclohexane Conversion (%)=[Molar amount of total product in terms of cyclohexane]/[Molar amount of prepared cyclohexane]×100

Product Yield (%)=[Molar amount of product in terms of cyclohexane]/[Molar amount of total product in terms of cyclohexane]×100

[Molar amount of total product in terms of cyclohexane]=[Total of the molar amount of product detected by GC (GC detected byproducts are measured as molar amounts in terms of cyclohexane)]+[Molar amount of TOC in terms of cyclohexane]+[Molar amount of CO and CO$_2$ in terms of cyclohexane]

From the results, the conversion of cyclohexane was 4.7%, the cyclohexanone yield was 15.9%, the cyclohexanol yield was 24.2%, and the cyclohexyl hydroperoxide yield was 44.4%.

Moreover, triphenyl phosphine was added to the abovementioned oxidation reaction solution, and the cyclohexyl hydroperoxide was converted to cyclohexanol, after which a 17 weight % sodium carbonate aqueous solution was added, and stirred and mixed at 155° C. for 120 minutes, and then the cyclohexanone and cyclohexanol in the oil phase and water phase were quantitatively determined. The total molar amount of cyclohexanone, cyclohexanol, and cyclohexyl hydroperoxide in the oxidizing liquid was subtracted from the total molar amount of cyclohexanone and cyclohexanol after the abovementioned treatment, and the other CxONOL precursor amount was calculated.

The CxONOL precursor in the oxidation reaction solution was 4.1 mol % with respect to the cyclohexyl hydroperoxide.

Next, the cyclohexane in the oxidation reaction solution was removed by distillation at a low temperature and reduced pressure, and the solution thereof was concentrated to 10-times.

The cyclohexyl hydroperoxide was then decomposed with the same conditions as those of Comparative Example 5 with the exception that the concentrated liquid of the abovementioned oxidation reaction solution was used as the press-in liquid of Comparative Example 1, and the reaction time was 40 minutes.

The cyclohexyl hydroperoxide decomposition percentage was 100%, and when the selectivity was calculated based on the definition of [Equation 1], the cyclohexanone selectivity was 72.2%, the cyclohexanol selectivity was 24.9%, and the total selectivity of both was 97.1%. However, when the selectivity was calculated based on the definition of [Equation 2], the cyclohexanone selectivity was 69.3%, the cyclohexanol selectivity was 23.9%, and the total selectivity of both was 93.2%. Moreover, the cyclohexanone/cyclohexanol production ratio was 2.90.

Example 10

The reaction solution of Comparative Example 9 was separated, and waste alkali was obtained. Eight grams of this waste alkali and 32 g of a 21.25 weight % sodium carbonate aqueous solution containing 50 weight ppm of Co were mixed, and 40 g of a 17 weight % sodium carbonate aqueous solution containing 40 ppm of Co was prepared. The cyclohexyl hydroperoxide was then decomposed with the same conditions as those of Comparative Example 9 with the exception that the alkaline aqueous solution was used as the water phase, and the reaction time was 30 minutes. The cyclohexyl hydroperoxide decomposition rate was 100%, and when the selectivity was calculated based on the definition of [Equation 1], the cyclohexanone selectivity was 73.6%, the cyclohexanol selectivity was 25.5%, and the total selectivity of both was 99.1%. On the other hand, when the selectivity was calculated based on the definition of [Equation 2], the cyclohexanone selectivity was 70.7%, the cyclohexanol selectivity was 24.5%, and the total selectivity of both was 95.2%. Moreover, the cyclohexanone/cyclohexanol production ratio was 2.89.

Example 11

Cyclohexyl hydroperoxide was decomposed with the same conditions as those of Example 10 with the exception that the reaction temperature was 140° C. and the reaction time was 14 minutes. The decomposition percentage of the cyclohexyl hydroperoxide was 100%, and when the selectivity was calculated based on the definition of [Equation 1], the cyclohexanone selectivity was 70.5%, the cyclohexanol selectivity was 26.1%, and the total selectivity of both was 96.7%. On the other hand, when the selectivity was calculated based on the definition of [Equation 2], the cyclohexanone selectivity was 67.6%, the cyclohexanol selectivity was 25.0%, and the total selectivity of both was 92.6%. Moreover, the cyclohexanone/cyclohexanol production ratio was 2.70.

Example 12

Cyclohexyl hydroperoxide was decomposed with the same conditions as those of Example 10 with the exception that the reaction temperature was 155° C. and the reaction time was 8 minutes. The decomposition percentage of the cyclohexyl hydroperoxide was 100%, and when the selectivity was calculated based on the definition of [Equation 1], the cyclohexanone selectivity was 67.5%, the cyclohexanol selectivity was 26.7%, and the total selectivity of both was 94.1%. On the other hand, when the selectivity was calculated based on the definition of [Equation 2], the cyclohexanone selectivity was 64.5%, the cyclohexanol selectivity was 25.5%, and the total selectivity of both was 90.0%. Moreover, the cyclohexanone/cyclohexanol production ratio was 2.53.

Comparative Example 10

Cyclohexyl hydroperoxide was decomposed with the same conditions as those of Comparative Example 9 with the exception that Co was not added and the reaction time was 320 minutes. The decomposition percentage of the cyclohexyl hydroperoxide was 100%, and when the selectivity was calculated based on the definition of [Equation 1], the cyclohexanone selectivity was 57.6%, the cyclohexanol selectivity was 32.2%, and the total selectivity of both was 89.8%. On the other hand, when the selectivity was calculated based on the definition of [Equation 2], the cyclohexanone selectivity was 55.3%, the cyclohexanol selectivity was 30.9%, and the total selectivity of both was 86.3%. Moreover, the cyclohexanone/cyclohexanol production ratio was 1.79.

The results of the abovementioned Comparative Example 9, Example 10 to 12 and Comparative Example 10 are shown in the following Table 3 (Comparison Table of CHP Decomposition Selectivity in the Oxidation Reaction Solution).

REFERENCE NUMERALS

A: hydroperoxide decomposition step
B: waste alkali separation step
D: alkali recovery step
1: oxidation reaction solution
2: aqueous solution containing alkaline earth metal carbonate or alkali metal carbonate and a transition metal compound
2-1: makeup of alkaline earth metal carbonate or alkali metal carbonate aqueous solution
2-2: makeup of transition metal compound aqueous solution
3: saponification liquid
4: waste alkali
4-1: waste alkali circulation
5: recovered alkali
6: water

What is claimed is:

1. A method for producing a ketone and/or alcohol having a same number of carbon atoms as a hydrocarbon compound by decomposing a hydroperoxide in a reaction solution obtained from oxidizing the hydrocarbon compound using molecular oxygen; wherein the method comprises:

a hydroperoxide decomposition step for decomposing the hydroperoxide into the ketone and/or alcohol by contacting the reaction solution with an aqueous solution into which a carbonate of an alkaline earth metal or a carbonate of an alkali metal and a transition metal compound are dissolved, wherein the hydroperoxide is decomposed in the aqueous solution;

a separation step for separating into an oil phase comprising the ketone and/or alcohol, and a water phase comprising the carbonate of an alkaline earth metal or carbonate of an alkali metal and the transition metal compound;

a water phase recycling step for recycling a part of the water phase to the hydroperoxide decomposition step;

a recovery step for recovering the carbonate of an alkali metal or carbonate of an alkaline earth metal and the transition metal compound by combusting at least a part of the remainder of the water phase; and an alkali recycling step for recycling to the hydroperoxide decomposition step by dissolving at least the carbonate of the alkali metal or the carbonate of the alkaline earth metal among the recovered substances obtained from the recovery step in water.

TABLE 3

| | Alkali | Co Concentration (ppm) | Waste Alkali Circulation Use | Reaction Temperature (° C.) | Reaction Time (min) | Decomposition Percentage (%) | Selectivity (%): [Equation 1] | | | Selectivity (%): [Equation 2] | | | ON/OL |
|---|---|---|---|---|---|---|---|---|---|---|---|---|---|
| | | | | | | | CxON | CxOL | CxONOL | CxON | CxOL | CxONOL | |
| Comparative Example 9 | 17% Na$_2$CO$_3$ | 40 | Not added | 125 | 40 | 100 | 72.2 | 24.9 | 97.1 | 69.3 | 23.9 | 93.2 | 2.90 |
| Example 10 | 17% Na$_2$CO$_3$ | 40 | 20% circulation | 125 | 30 | 100 | 73.6 | 25.5 | 99.1 | 70.7 | 24.5 | 95.2 | 2.89 |
| Example 11 | 17% Na$_2$CO$_3$ | 40 | 20% circulation | 140 | 14 | 100 | 70.5 | 26.1 | 96.7 | 67.6 | 25.0 | 92.6 | 2.70 |
| Example 12 | 17% Na$_2$CO$_3$ | 40 | 20% circulation | 155 | 8 | 100 | 67.5 | 26.7 | 94.1 | 64.5 | 25.5 | 90.0 | 2.53 |
| Comparative Example 10 | 17% Na$_2$CO$_3$ | Not added | Not added | 125 | 320 | 100 | 57.6 | 32.2 | 89.9 | 55.3 | 30.9 | 86.3 | 1.79 |

2. The production method according to claim 1, further comprising a concentration step for concentrating the water phase between the separation step and the recovery step.

3. The production method according to claim 1, wherein the pH of the water phase is more than or equal to 7.5 and less than or equal to 12.

4. The production method according to claim 1, wherein the transition metal compound includes at least one transition metal selected from a group comprising group 6A, group 7A, and group 8 of the periodic table of elements.

5. The production method according to claim 1, wherein the transition metal compound includes at least one transition metal selected from a group including chromium, manganese, iron, cobalt, nickel, copper, ruthenium, rhodium, palladium, and platinum.

6. The production method according to claim 1, wherein the transition metal compound is at least one compound selected from a group including mineral acid salts, carboxylates, carbonates, basic carbonates, hydroxides, oxides, and complexes.

7. The production method according to claim 1, wherein the hydrocarbon compound is cyclohexane, and the hydroperoxide is cyclohexyl hydroperoxide.

8. A system for producing a ketone and/or alcohol having a same number of carbon atoms as the hydrocarbon compound by decomposing a hydroperoxide in a reaction solution obtained from oxidizing the hydrocarbon compound using molecular oxygen, wherein the system comprising:

a hydroperoxide decomposition unit for decomposing the hydroperoxide into a ketone and/or alcohol by contacting the reaction solution with an aqueous solution into which a carbonate of an alkaline earth metal or a carbonate of an alkali metal and a transition metal compound are dissolved, wherein the hydroperoxide is decomposed in the aqueous solution, and;

a separation unit for separating into an oil phase comprising the ketone and/or alcohol, and a water phase comprising the carbonate of an alkaline earth metal or carbonate of an alkali metal and the transition metal compound;

a water phase recycling unit for recycling a part of the water phase to the hydroperoxide decomposition unit;

a recovery unit for recovering the carbonate of an alkali metal or carbonate of an alkaline earth metal and the transition metal compound by combusting at least a part of the remainder of the water phase, an alkali recycling unit for recycling to the hydroperoxide decomposition unit by dissolving at least the carbonate of the alkali metal or the carbonate of the alkaline earth metal among the recovered substances obtained from the recovery unit in water.

* * * * *